United States Patent [19]

Lee

[11] Patent Number: 5,236,693
[45] Date of Patent: Aug. 17, 1993

[54] MEDICAL ULTRASOUND CONTRAST AGENT AND METHOD OF USING SAME

[75] Inventor: Richard T. Lee, Weston, Mass.

[73] Assignee: Brigham and Women's Hospital, Boston, Mass.

[21] Appl. No.: 612,855

[22] Filed: Nov. 14, 1990

[51] Int. Cl.$^5$ .............................................. A61K 49/00
[52] U.S. Cl. ..................................... 424/9; 128/653.1
[58] Field of Search .......................... 424/9; 128/653.1

[56] References Cited

U.S. PATENT DOCUMENTS

| | | | |
|---|---|---|---|
| 4,247,406 | 1/1981 | Widder et al. | 424/1 |
| 4,265,251 | 5/1981 | Tickner | 128/660 |
| 4,657,756 | 4/1987 | Rasor et al. | 424/9 |

FOREIGN PATENT DOCUMENTS

| | | |
|---|---|---|
| 0184899 | 10/1985 | European Pat. Off. |
| 0186947 | 10/1985 | European Pat. Off. |
| PCT/US84/-00135 | 1/1984 | PCT Int'l Appl. |

OTHER PUBLICATIONS

Smith et al. "Superior Intensity and Reproducibility of SHU-454 . . . " J. Am. Coll. Cardiol., 1984 (Apr.), vol. 3(4), pp. 992-998; abstract in Medline AN 84163099.
Smith et al., "Left Heart Opacification . . . " J. Am. Coll. Cardiol., 1989 (Jun.) vol. 13(7), pp. 1622-1628; abstract in Medline AN 89256357.
Shapiro, J. R. et al. *JACC* 13:1629-30 (1989), No. 7.
Lindberg, B. et al., Microspheres and Drug Therapy, Pharmaceutical, Immunological and Medical Aspects, Chapter 1:153-188 (1984), Elsevier Sc. Pub. B.V.
Tuma, R. F., Microspheres and Drug Therapy, Pharmaceutical, Immunological and Medical Aspects, Chapter 2:189-203 (1984) Elsevier Sc. Pub. B.V.

*Primary Examiner*—Richard L. Raymond
*Assistant Examiner*—John D. Pak
*Attorney, Agent, or Firm*—Sterne, Kessler, Goldstein & Fox

[57] ABSTRACT

A medical ultrasound contrast agent and method of using the same wherein the contrast agent comprises a pharmaceutically acceptable carrier in combination with a substantially solid, radioactively opaque, biodegradable particle. The particle is of a size allowing it to be passed through the lungs to the left side of the heart where it may be visualized by conventional medical ultrasound.

5 Claims, 1 Drawing Sheet

MEDICAL ULTRASOUND CONTRAST AGENT AND METHOD OF USING SAME

FIELD OF THE INVENTION

The present invention relates to a medical ultrasound contrast agent and method of using the same, and more particularly to a medical ultrasound contrast agent that is completely biodegradable and that is capable of passing through the small blood vessels of the lungs to allow ultrasonic imaging of the left side of the heart.

BACKGROUND OF RELATED ART

In a normal human being, blood flows from the veins of the body to the right heart chambers. The blood then passes through the lungs (where the red cells pick up oxygen), back to the left heart chambers, and then out of the left heart through the aorta. This sequence of blood flow and the passage through which the blood moves through the body can be studied by ultrasonic imaging, a conventional technique which translates the reflection of sound waves into a visual image. Over the past decade, there has been an interest in cardiology in the development of an ultrasonic contrast agent that is capable of passing through the small vessels of the lungs. An ultrasound contrast agent capable of passing through the small blood vessels of the lungs would allow study of the left side of the heart with conventional medical ultrasound technology, e.g. echocardiography or vascular ultrasound.

One common and clinically useful method of studying the right heart chambers involves the injection of small bubbles, created by shaking or agitating liquid, into the cardiovascular system. These bubbles are generally larger than 10 microns. Although these microbubbles are easily visualized by ultrasound in the right heart chambers, they are filtered out by the capillaries of the lungs and, thus, are not transferred to the left heart chambers. Therefore, they can not and do not enhance ultrasound imaging of the left heart chambers. Two contrast agents are currently under investigation in the United States which also create small microbubbles that are allegedly able to pass through the lungs. However, these microbubbles have been known to pass back into solution under the high pressure of the left heart, and neither agent has been approved by the FDA for general use. See, Shapiro, J. R. et al., "Prospects of Transpulmonary Contrast Echocardiography," The American College of Cardiology, No. 0735-1097 (1989).

Another example of an ultrasound contrast agent is described in PCT International Application No. PCT/US84/00135 by Feinstein. This application discloses a method of ultrasonic imaging which comprises injecting microparticles or sonicated microbubbles into the circulatory system of an animal or human. The microparticles are formed from an amino acid polymer matrix with magnetic particles embedded therein to reflect intense patterns of ultrasonic waves. While such particles may enhance ultrasonic imaging, they are not biodegradable.

Similarly, a paramagnetic contrast agent for nuclear magnetic resonance and ultrasound is disclosed in European patent application, publication nos. 0186947 and 0184899. This agent uses as a carrier, a water-insoluble macro molecular material comprising a polymeric or polymerized carbohydrate or a polymerized sugar alcohol or derivative therof. These disclosures do not disclose an ultrasonic contrast agent that is biodegradable.

One important use of a left heart ultrasonic imaging agent is in the diagnosis of coronary artery disease, the major cause of death in developed countries. The coronary arteries arise from the aorta and feed the heart muscle. When coronary artery disease blocks blood flow to a portion of the heart, that portion of the heart is in danger. Currently, thallium nuclear scintigraphy is the only noninvasive method of evaluating myocardial blood flow. Thallium scintigraphy is expensive, requires a nuclear isotope, and does not give an evaluation of cardiac performance (as an ultrasound image does).

Thus, the need exists for an ultrasound contrast agent that is safe, reliable, biodegradable and that enhances visualization of vascularized organs and typcially the left heart.

SUMMARY OF THE INVENTION

The present invention is directed to methods for enhancing ultrasound images of vascularized organs within an animal body using biodegradable, echogenic, size-selected particles, and pharmaceutical compositions for effecting same. In a preferred embodiment, the biodegradable, echogenic, size-selected particles are starch microspheres having a diameter of 7 to 8 microns and find particular utility in ultrasonic visualizing of the heart, and preferably the left chambers of the heart.

With the ultrasonic contrast agent of the present invention, myocardial contrast is possible through simple intravenous injection. Furthermore, because the contrast imaging agent of the present invention is capable of passing through the lungs, it is possible to observe areas of the heart exhibiting different amounts of blood flow by examining their different intensities under ultrasonic imaging.

The contrast agent of the present invention, therefore, has a number of uses. One example is the study of the effects of exercise or medications on the blood supply to the heart. In addition, this agent is useful for diagnosis of many congenital abnormalities in the cardiac structure. Other uses include visualizing the left ventricle or heart chamber; and visualizing the myocardium or heart muscle as the contrast agent enters the blood vessels of the heart muscle (commonly termed perfusion imaging).

BRIEF DESCRIPTION OF THE DRAWING

The foregoing and other objects, aspects, features and advantages of the present invention will be more fully appreciated as the same become better understood from the following detailed description of the present invention when considered in conjunction with the accompanying drawing, in which.

DETAILED DESCRIPTION

Figure 1:
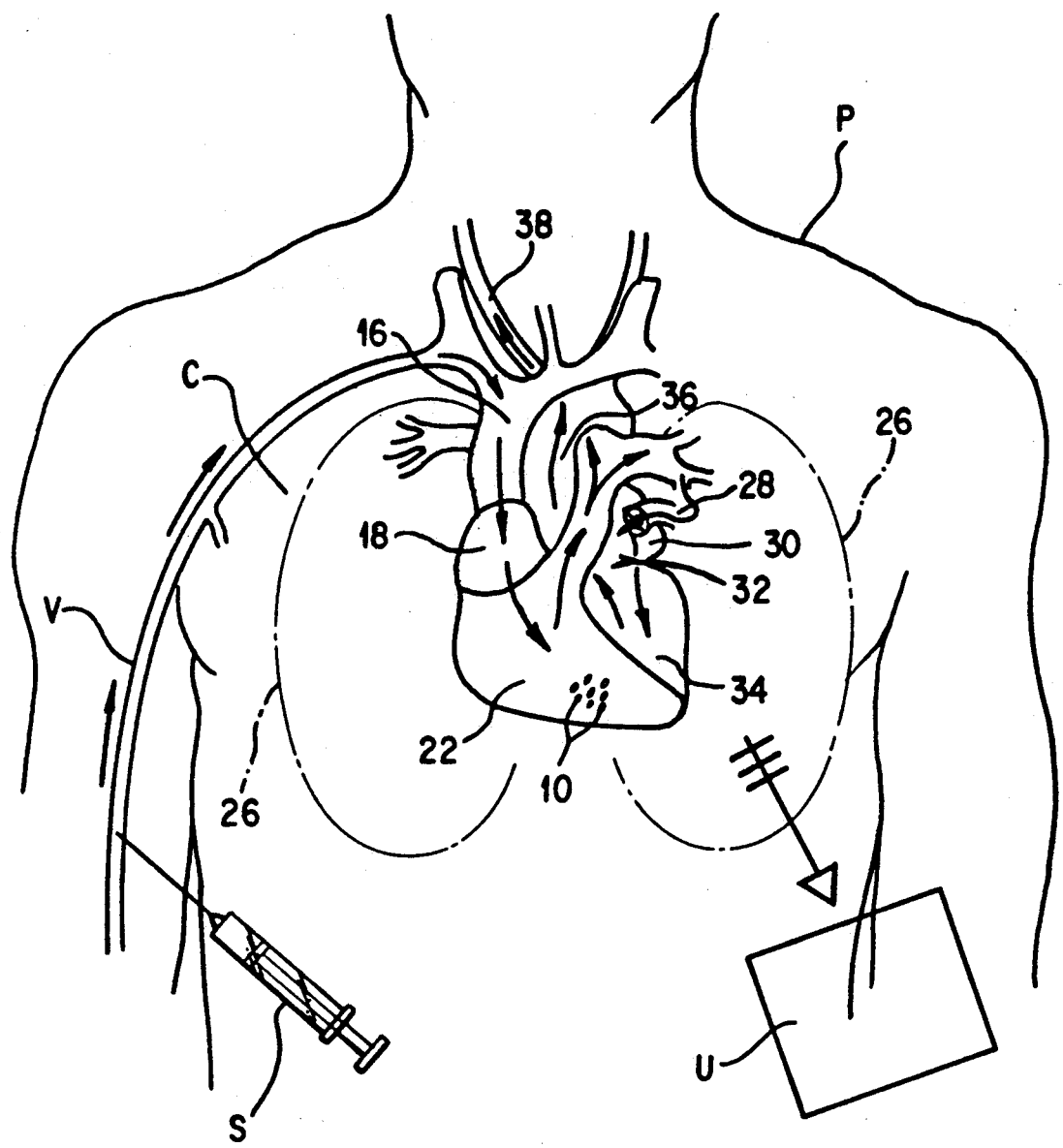
FIG. 1 is a schematic diagram of the cardiovascular system of a human being showing how the contrast agent of the present invention is introduced into the system and how an image of the system is created.

With reference to FIG. 1, the present invention comprises a contrast agent for introduction into the circulatory system of a patient P. Although a human patient is shown in the drawing, it should be understood that the present invention is not limited to use in a human being but is adapted for use with all animals having a circulatory system. The present invention enhances a ultrasonic imaging of blood flow through the circulatory system of an animal.

In particular, the contrast agent of the present invention comprises inert particles or microspheres in combination with a pharmaceutically acceptable carrier which is adapted for introduction into the circulatory system of the animal. Each particle, as shown in the drawing Figure as 10, is echogenic (i.e. opaque to ultrasound and capable of reflecting sound waves), and therefore, acts as a contrast agent when visualized using conventional medical ultrasound techniques, for example echocardiography and vascular ultrasound at a frequency of 2.5 to 5 MHZ. The particles are preferably spherical shaped, although other shapes are possible. In a preferred embodiment, the particles comprise a cross-linked starch, for example potato starch. However, other suitable substances for forming the particles exist. European patent application nos. 0184899 and 0186947, which are incorporated in their entirety herein by reference, describe several examples of suitable polymeric or polymerized carbohydrate or polymerized sugar alcohol or derivative suitable for use as an echogenic particle in the present invention. The entire particle is completely biodegradable in the body, typically by serum amylase, a naturally occurring enzyme found in the body.

The particles are substantially solid and may in some instances be completely solid. The preferred diameter of spherically shaped particles is four (4) to nine (9) microns, most preferred being seven (7) to eight (8) microns. Tests have successfully been performed using particles having a diameter as small as three (3) microns to six (6) microns. One example of an acceptable microsphere is DSM (degradable starch microsphere) available from Pharmacia LEO Therapeutics AB in Uppsala, Sweden. Microshperes having a diameter of 5.6 microns are available from Pharmacia under the designation of DSM Batch No. BR71B06B. Other than experiments related to the present invention and those described in European patent application nos. 0184899 and 0186947 described above, it is believed that similar microshperes have been used experimentally mentally as a means of controlled drug delivery to cancers (e.g. tumors).

As mentioned above, the particles are suspended in a carrier or fluid that is capable of being introduced into the circulatory system of an animal. The microspheres swell in the carrier and exhibit gel characteristics making them slightly deformable. Thus, they can adapt their shape to the vascular cavities of the body. Any pharmaceutically acceptable carrier may be employed for this purpose. Examples include conventional saline, water and intravenous fluid. The concentration of particles to carrier should preferably be within the range of 25 to 1,000 micrograms per milliliter, with the most preferred concentration for the average human being 250 micrograms per milliliter.

In use, the contrast agent is prepared by mixing a predetermined amount of bio-degradable particles in a suitable amount of carrier. The agent may be prepared in advance of the procedure and stored until use, or may be prepared in contemplation of the procedure and used immediately. In either case, the prepared agent is transferred to a conventional syringe or other suitable apparatus for administering fluid to the circulatory system (e.g. a catheter). If a syringe is used, the contrast agent is introduced into the circulatory system by injecting the needle into a vein. When the patient is a human, as shown in the Figure, introduction is preferably through an arm vein V using a conventional syringe S.

Referring to the Figure in which the cardiovascular system of a human is shown in a detailed schematic, the contrast agent travels through the circulatory system towards the heart. Upon reaching the heart, the contrast agent first enters the superior vena cava 16 which leads to the right side of the heart. The contrast agent enters the right side of the heart through the right atrium 18 and passes through the tricuspid valve into the right ventricle 22. From the right ventricle, the contrast agent is passed to the lungs 26 through the pulmonary artery 24. In the lungs 26, the contrast agent is passed through the capillaries and back into the pulmonary vein 28. This is an important feature of the present invention because it allows the contrast agent to aid in visualization of the left side of the heart. In order to enhance an ultrasonic image of the left side of the heart, it is important that the particles be of a size that allows them to pass through the capillaries to the pulmonary vein and ultimately to the left side of the heart. From the pulmonary vein 28, the contrast agent is passed to the left atrium 30. From the left atrium, the contrast agent passes through the mitral valve 32 to the left ventricle 34. From the left ventricle 34, the contrast agent passes to the left coronary artery 36 and the aorta 38 into the veins of the body where it is eventually degraded by serum amylase.

While the contrast agent is making its way through the circulatory system of patient P, a conventional medical ultrasound device U is preferably disposed adjacent the chest C of the patient. The medical ultrasound device U is positioned to provide ultrasonic images of the heart of patient P.

The contrast agent of the present invention is capable of providing enhanced visualization of vascularized organs of the body, and in particular, the chambers of the heart (i.e. the right atrium, the right ventricle, the left atrium and the left ventricle) because they are opaque to ultrasonic signals and they are able to conform to the vascular contours. When the contrast agent of the present invention is used to image the cardiovascular system, the shape and contour of the heart chambers are revealed, as well as an indication of any abnormalities and, or blockages in the system.

In most patients diagnosed with heart disease, the left ventricle of the heart exhibits the greatest irregularities. Therefore, it is an especially beneficial feature of the present invention that the particles of the contrast agent are of a size that allows them to be passed to the left side of the heart and into the left ventricle to permit enhanced visualization of the left ventricle. As noted above, this feature is possible with the present invention because the particles of the present invention are of a size capable of passing safely through the lungs, while at the same time being echogenic.

In addition, the present invention also allows enhanced visualization of vascularized organs, for example, the myocardium or heart muscle. That is, the contrast agent present within the blood in the heart muscle has been shown to give a sparkling appearance when visualized using conventional medical ultrasound. This perfusion imaging technique allows study of problems associated with the heart muscle itself.

Furthermore, the present invention can be used to study the effect of exercise or medication on the blood supply to the heart. To accomplish such a study, one fellows the method outlined above with regard to administering the contrast agent to the circulatory system and preserves the ultrasound image, for later comparison, by any known technique. The patient is then exposed to exercise or medication that is believed to have an effect on blood flow in the circulatory system. The method of administration and imaging is repeated and the first image taken before exposure to the blood flow effecting activity is compared to the second image taken after such activity. Any blockage present in the heart chambers due to the activity would be apparent by comparing the two images. For example, during exercise, a portion of the heart may not develop an ultrasonic contrast appearance because blood is not flowing to that portion of the heart during exercise. After waiting for the cardiovascular status to return to a rest condition, a second image might reveal that that same portion of the heart does have an ultrasonic contrast appearance at rest. This comparison would be evidence that that portion of the heart is not receiving blood during exercise, although it does receive blood at rest. Such a finding would be because most patients with coronary artery disease have adequate blood flow to the heart at rest, but have inadequate blood flow to certain regions of the heart during exercise.

In addition to enhancing ultrasonic imaging of the cardiovascular system, the present invention may also be used to image other bodily organ systems such as the liver, spleen, and kidney.

It should be understood that the foregoing disclosure relates only to presently preferred embodiments, and that it is intended to cover all changes and modifications of the invention herein chosen for the purpose of the disclosure which do not constitute departures from the spirit and scope of the invention as set forth is the appended claims.

What I claim is:

1. A method of enhancing ultrasonic imaging of a vascularized organ in an animal, comprising the steps of:
   introducing a contrast composition into the circulatory system of said animal, said contrast composition consisting essentially of a pharmaceutically acceptable carrier and an effective amount of an insoluble cross-linked starch particle of a size to produce ultrasonic imaging; and
   ultrasonically imaging said particle within said vascularized organ.

2. The method set forth in claim 1, further including the step of:
   suspending said particle in said pharmaceutically acceptable carrier before it is introduced into said animal.

3. The method set forth in claim 2, further comprising the step of:
   ultrasonically imaging said particle within a portion of the cardiovascular system of said animal to observe passage of the particle through the circulatory system into the left atrium and left ventricle of the heart.

4. The method set forth in claim 3, further comprising the step of:
   altering the blood flow in said circulatory system after said step of ultrasonically imaging said particle within the said portion of the cardiovascular system.
   re-introducing said contrast composition into said circulatory system;
   re-imaging said particle within said portion of the cardiovascular system; and
   comparing the observations made during the step of imaging, with those made during the step of re-imaging, to study the effect of altering the blood flow on said cardiovascular system of said animal.

5. The method set forth in claim 1, wherein said step of ultrasonically imaging said particle is performed simultaneously with said step of introducing said contrast composition.

* * * * *